US010092387B2

(12) United States Patent
Tai et al.

(10) Patent No.: US 10,092,387 B2
(45) Date of Patent: Oct. 9, 2018

(54) IMPLANTABLE DEVICE FOR RETAINING LIVE CELLS AND PROVIDING NUTRIENTS THERETO

(71) Applicants: California Institute of Technology, Pasadena, CA (US); City of Hope, Duarte, CA (US)

(72) Inventors: Yu-Chong Tai, Pasadena, CA (US); Dongyang Kang, Pasadena, CA (US); Hirotake Komatsu, Duarte, CA (US); Henry K. Lin, Pasadena, CA (US); Yoko Mullen, Sherman Oaks, CA (US)

(73) Assignees: California Institute of Technology, Pasadena, CA (US); City of Hope, Duarte, CA (US)

( * ) Notice: Subject to any disclaimer, the term of this patent is extended or adjusted under 35 U.S.C. 154(b) by 0 days.

(21) Appl. No.: 15/274,229

(22) Filed: Sep. 23, 2016

(65) Prior Publication Data
US 2017/0086963 A1      Mar. 30, 2017

Related U.S. Application Data

(60) Provisional application No. 62/222,913, filed on Sep. 24, 2015.

(51) Int. Cl.
*A61F 2/02*   (2006.01)
*C12M 1/00*   (2006.01)

(52) U.S. Cl.
CPC ............. *A61F 2/022* (2013.01); *C12M 21/00* (2013.01); *A61F 2240/004* (2013.01)

(58) Field of Classification Search
CPC .... A61F 9/0017; A61F 2/022; A61M 5/14276
See application file for complete search history.

(56) References Cited

U.S. PATENT DOCUMENTS 7,186,232 B1    3/2007  Smedley et al.
8,986,727 B2    3/2015  Martin et al.
(Continued)

FOREIGN PATENT DOCUMENTS

WO      2014055989      4/2014

OTHER PUBLICATIONS

International Search Report and Written Opinion dated Dec. 27, 2016 for corresponding PCT Application No. PCT/US2016/053372 filed Sep. 23, 2016, 7 pages.
(Continued)

*Primary Examiner* — Nathan R Price
*Assistant Examiner* — Justin L Zamory
(74) *Attorney, Agent, or Firm* — Kilpatrick Townsend & Stockton LLP

(57) ABSTRACT

An implantable medical device, a method of manufacturing, and a method of use are described. The implantable medical device includes an absorption bag connected by a cannula to a discharge bag. The implantable medical device also includes a reservoir external to the discharge bag and attached to a surface of the discharge bag. At least a portion of the absorption bag and at least a portion of a bottom surface of the reservoir are permeable to a predefined class of small molecules, such as molecular oxygen. The reservoir can retain live cells that rely on the small molecules for survival and growth. Based on concentration of the small molecules, the small molecules permeate into the absorption bag and are transported to the discharge bag for permeation into the reservoir, thereby providing a supply of the small molecules to the live cells.

17 Claims, 9 Drawing Sheets

(56) References Cited

U.S. PATENT DOCUMENTS

| | | | |
|---|---|---|---|
| 2002/0103475 A1* | 8/2002 | Bartha | A61M 5/14276 604/891.1 |
| 2004/0147871 A1 | 7/2004 | Burnett et al. | |
| 2007/0135829 A1 | 6/2007 | Paganon | |
| 2008/0181930 A1* | 7/2008 | Rodstrom | A61F 9/0017 424/427 |
| 2009/0012502 A1 | 1/2009 | Rotem et al. | |
| 2010/0130916 A1 | 5/2010 | Stern et al. | |
| 2010/0196439 A1 | 8/2010 | Beck et al. | |
| 2011/0054387 A1 | 3/2011 | Stern et al. | |
| 2014/0236078 A1 | 8/2014 | Dalton | |
| 2014/0242123 A1* | 8/2014 | Guan | A61K 47/42 424/400 |
| 2015/0366707 A1 | 12/2015 | Park et al. | |

OTHER PUBLICATIONS

Abdallah et al., "Vitreal Oxygenation in Retinal Ischemia Reperfusion," Invest Ophthalmol. Vis. Sci., vol. 52, No. 2, Feb. 2011, pp. 1035-1042.

Balachandran et al., "Contribution of Saccadic Motion to Intravitreal Drug Transport," Pharm Res, vol. 28, 2011, pp. 1049-1064.

Barbazetto et al., "Oxygen tension in the rabbit lens and vitreous before and after vitrectomy," Experimental Eye Research, vol. 78, 2004, pp. 917-924.

Chawla et al., "Biodegradable and Biocompatible Synthetic Saccharide-Peptide Hydrogels for Three-Dimensional Stem Cell Culture," Biomacromolecules, vol. 12, No. 3, Mar. 14, 2011, 18 pages.

Chin et al., "Hydrogel-Perfluorocarbon Composite Scaffold Promotes Oxygen Transport to Immobilized Cells," Biotechnol. Prog., vol. 24, No. 2, 2008, pp. 358-366.

Clarkson et al., "Natural History and Clinical Management of Central Retinal Vein Occlusion," Arch Ophthalmol., vol. 115, 1997, pp. 486-491.

Congdon et al., "Causes and Prevalence of Visual Impairment Among Adults in the United States," Arch Ophthalmol., vol. 122, 2004, pp. 477-485.

Eison-Perchonok et al., "Kinetics of Ascorbic Acid Autoxidation as a Function of Dissolved Oxygen Concentration and Temperature," Journal of Food Science, vol. 47, 1982, pp. 765-767.

Filas et al., "Computational Model for Oxygen Transport and Consumption in Human Vitreous," Invest. Ophthalmol Vis Sci., vol. 54, 2013, pp. 6549-6559.

Goto et al., "Frequency and Risk Factors for Neovascular Glaucoma After Vitrectomy in Eyes with Proliferative Diabetic Retinopathy," J. Glaucoma, vol. 22, No. 7, Sep. 2013, pp. 572-576.

Hayreh, "Management of Central Retinal Vein Occlusion," Ophthalmologica, vol. 217, May/Jun. 2003, pp. 167-188.

Kampen et al., "The Prevalence of Diabetic Retinopathy Among Adults in the United States," Arch Ophthalmol., vol. 122, 2004, pp. 552-563.

Kang et al., "MEMS Oxygen Transporter to Treat Retinal Ischernia," Micro Electro Mechanical Systems (MEMS), 2015 $28^{th}$ IEEE International Conference on Jan. 18-22, 2015.

Kim et al., "Mathematical Analysis of Oxygen Transfer Through Polydimethylsiloxane Membrane Between Double Layers of Cell Culture Channel and Gas Chamber in Microfluidic Oxygenator," Microfluidics and Nanofluidics, vol. 15, 2013, pp. 285-296.

Klein et al., "The 15-Year Cumulative Incidence of Retinal Vein Occlusion," Arch Ophthalmol., vol. 126, No. 4, 2008, pp. 513-518.

Landers et al., "Panretinal Photocoagulation and Retinal Oxygenation," Retina, vol. 2, 1982, pp. 167-175.

Liao et al., "Maintaining Functional Islets through Encapsulation in an Injectable Saccharide-Peptide Hydrogel," Biomaterials., vol. 34, No. 16, May 2013, pp. 3984-3991.

Luan et al., "Long-Term Allogeneic Islet Graft Survival in Prevascularized Subcutaneous Sites Without Immunosuppressive Treatment," American Journal of Transplantation, vol. 4, 2014, pp. 1533-1542.

McIntosh et al., "Natural History of Central Retinal Vein Occlusion: An Evidence-Based Systematic Review," Ophthalmology, vol. 117, 2010, pp. 1113-1123.

Pedraza et al., "Preventing hypoxia-induced cell death in beta cells and islets via hydrolytically activated, oxygen-generating biomaterials," PNAS, vol. 109, No. 11, Mar. 13, 2012, pp. 4245-4250.

Raoof et al., "Electrocatalytic Determination of Ascorbic Acid at Chemically Modified Carbon Paste Electrode with 2, 7-bis (Ferrocenyl ethynyl) Fluoren-9-one," Int. J. Electrochem. Sci, vol. 2, 2007, pp. 534-548.

Roos, "Theoretical estimation of retinal oxygenation during retinal artery occlusion," Physiol. Meas., vol. 25, 2004, pp. 1523-1532.

Roy et al., "The Prevalence of Diabetic Retinopathy Among Adult Type 1 Diabetic Persons in the United States," Arch Ophthalmol., vol. 122, 2004, pp. 546-551.

Shui et al., "The Gel State of the Vitreous and Ascorbate-Dependent Oxygen Consumption," Arch Ophthalmol., vol. 127, No. 4, 2009, pp. 475-482.

Stocchino et al., "Eye rotation induced dynamics of a Newtonian fluid within the vitreous cavity: the effect of the chamber shape," Phys. Med. Bioi., vol. 52, 2007, pp. 2021-2034.

Sweets et al., "Glucose-Stimulated Increment in Oxygen Consumption Rate as a Standardized Test of Human Islet Quality," American Journal of Transplantation, vol. 8, Jan. 2008, pp. 183-192.

* cited by examiner

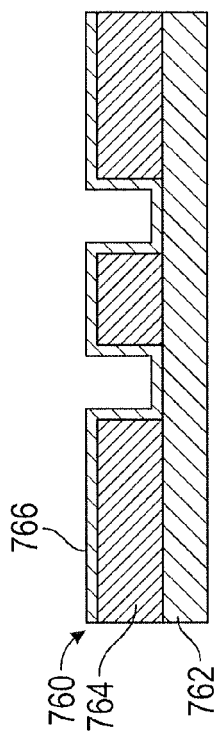
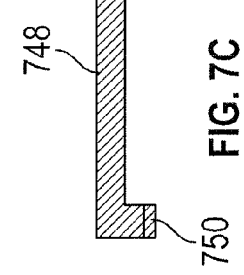
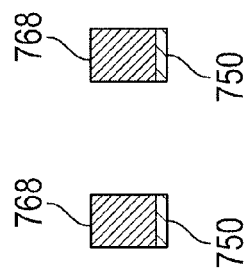
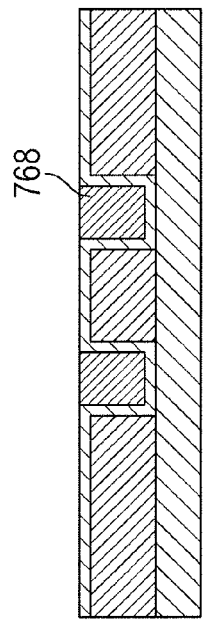
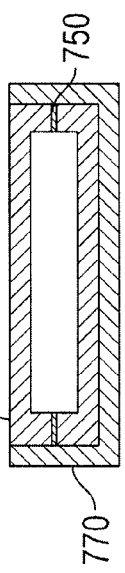

IMPLANTABLE DEVICE FOR RETAINING LIVE CELLS AND PROVIDING NUTRIENTS THERETO

CROSS-REFERENCES TO RELATED APPLICATIONS

This application claims the benefit of U.S. Provisional Application No. 62/222,913, filed Sep. 24, 2015, the contents of which are hereby incorporated in its entirety for all purposes.

BACKGROUND

1. Field of the Art

Generally, embodiments of the present invention relate to methods and devices for implanting live cells within a body and providing nutrients to the live cells. The nutrients can be transported from an environment external to the body or from within the body.

2. Description of the Related Art

Diabetes is a group of widespread diseases in which there are high blood sugar levels over a prolonged period. If left untreated, diabetes can cause many complications. Acute complications can include diabetic ketoacidosis, nonketotic hyperosmolar coma, or death. Serious long-term complications include heart disease, stroke, chronic kidney failure, foot ulcers, and damage to the eyes. Diabetes is due to either cells in the pancreas not producing insulin (type-I diabetes) or not responding properly with the insulin production and release (type-II diabetes).

Pancreatic islets or islets of Langerhans, referred to herein as islets, are clusters of cells, containing mostly beta cells that secrete insulin. In people suffering from type-I diabetes, the islets are destroyed. One of medical solutions is to implant islets. In islet transplantation, cells are isolated from a donor pancreas and transplanted into type I diabetic patients. Once implanted, the transplanted islets begin to make and release insulin, thereby helping patients potentially avoiding the need of daily insulin injections.

Islet transplantation into the liver of diabetic patients has been studied for decades as a long-term treatment of type-I diabetes by normalizing blood sugar levels and preventing life-threatening hypoglycemic episodes. However, this "intrahepatic" islet transplantation results in chronic decline of islet function due to inflammation, immune response, and toxic environment to islets.

Attempts have been made to transplant islets into sites outside the liver. For example, the subcutaneous site (e.g., under the skin) is promising as it provides a large area and easy access for transplantation. However, low oxygen supply to implanted islets within the subcutaneous microenvironment is detrimental to islet survival. Specifically, the survival of islets depends on sufficient supply of oxygen to the islets at the site of implantation. Inadequate flow of oxygen, and/or of other nutrients, leads to the death of the islets, thereby negating any benefits of the implantation.

For a period of time after a subcutaneous implantation, a risk for ischemia exists. Ischemia is caused by inadequate blood flow due to the lack of adequate vascular structure in the subcutaneous implantation site. Oxygen supply to the implanted islets is not proper until sufficient vascular growth is achieved around the islets. Accordingly, for the islets to survive during the period of time between implantation and vascular growth, oxygen should be adequately supplied from other sources. No solutions exist currently for the adequate oxygen supply in islet transplantation outside of the liver.

Therefore, current treatments of diabetes based on islet implantation have a number of distinct disadvantages that need to be overcome.

BRIEF SUMMARY

Generally described is a microfabricated, implantable medical device with two bags connected by an impermeable cannula in the middle, where one of the bags is configured to retain live cells on its external surface. The implantable medical device is used to implant the live cells, such as islets, in an implantation site, such as a subcutaneous site and provide nutrients to the live cells, thereby enabling their survival.

In an embodiment, one of the bags is fully or partially permeable to a predefined class of small molecules of interest, such as diatomic oxygen ($O_2$) or other "drugs." The small molecules generally provide nutrients to the live cells. This bag is referred to herein as an absorption bag. Specifically, the permeability of the absorption bag enables permeation of the small molecules from a surrounding environment into the absorption bag. The other bag is partially permeable to the small molecules, where the permeation is at a specific location of the bag. This bag is referred to herein as a discharge bag. Specifically, the live cells are retained on an external surface of the discharge bag, where the external surface corresponds to (e.g., includes or consists of) the permeation area of the discharge bag. The small molecules are transported from the absorption bag to the discharge bag via the cannula and permeates through the permeation area to the live cells.

The bags can be sized to collect and disburse an estimated amount of the small molecules and transfer them by passive means, that is, by virtue of there being a higher concentration of the molecules in one region than another region. Proteins to assist in the capture and transport of the target small molecule can also be included within the device.

The cannula can include a tube or strip of pliable, bendable material, such as metal, so that a surgeon can bend the cannula and keep it bent in order to align the device in the body. For example, the device can be mounted so that its cannula enters the subcutaneous site and bends back so that the discharge bag sits below the skin. Suture holes can be included to assist implantation.

Also described are methods of microfabrication of the device from biocompatible silicone and parylene. Microfabrication can include using custom molds. Cavities in the molds can define the bags, cannula, and reservoir. The reservoir-related molds can be customized to retain a certain amount of the live cells for implantation. The bag and/or cannula-related molds can be customized based on an estimated consumption of small molecules by the live cells, such that adequate amounts of the small molecules can be provided to the live cells during a period of time. Not only can the size be customized depending on the estimated consumption, but the thickness and/or permeability of the bags can also be customized.

In an embodiment, the implantable medical device includes an absorption bag, a cannula, a discharge bag. At least a portion of the absorption bag is permeable to a predefined class of small molecules, such as molecule oxygen. A first portion of the discharge bag is permeable to the small molecules, whereas a second portion (e.g., the remaining portion) of the discharge bag is impermeable to the small molecules. The cannula includes a lumen. The lumen is impermeable to the small molecules and connects an interior of the absorption bag to an interior of the discharge bag. The implantable medical device also includes a means for retaining live cells and for providing the small molecules to the live cells based on permeation through the first portion of the discharge bag. Permeable and impermeable portions can be defined by using specific materials. Various materials are available and are biocompatible and/or biodegradable. For instance, silicone is used to define permeable portions. A coating of parylene is used to reduce the permeability and, thus, define impermeable portions. The absorption bag and the discharge bag have approximately a same shape, such as cylindrical shape or a torus with a mesh connecting opposite points of the torus. For cylindrical shapes, internal diameters in the range of 2 mm to 30 mm and internal heights in the range of 200 µm to 2 mm can be used.

For example, the means includes a reservoir. The reservoir is external to the discharge bag and that includes a wall, an opening, and a bottom. The wall is impermeable to the small molecule and is attached to the first portion of the discharge bag. The bottom is defined by the first portion of the discharge bag. The reservoir is configured to retain live cells received through the opening and to provide the small molecules (e.g., oxygen) to the live cells based on permeation of the small molecules through the first portion of the discharge bag. The discharge bag and the absorption bag are dimensioned based on an expected consumption of the small molecules by the live cells. The reservoir can have a cylindrical shape. Its internal diameters is in the range of 1 mm to 20 mm. Its height falls in the range of 100 µm to 1 mm.

In another example, the means includes an irregular array of corrugations that are disposed on an external side of the first portion of the discharge bag. In yet another example, the means includes a pattern of corrugations that are disposed on an external side of the first portion of the discharge bag. In a further example, the live cells are included in a culture, such as a hydrogel. The means includes an adhesion layer between the first portion of the discharge bag and the hydrogel.

In addition, the culture is added to the means and the small molecules (e.g., oxygen) permeates to the culture through the first portion of the discharge bag.

In an example, the live cells include islets and the culture includes hydrogel. In this example, the hydrogel includes vinyl sulfone and cysteine.

In an embodiment, a method of manufacturing an implantable medical device is described. The method includes spreading a uncured, biocompatible silicone on half molds. The method also includes partially curing the uncured, biocompatible silicone on the half molds to create partially cured silicone halves. The method also includes aligning and joining the partially cured halves to create a partially cured silicone workpiece. The partially cured silicone workpiece defines an absorption bag connected by a cannula to a discharge bag. The method also includes aligning and joining at least one partially cured silicone piece with an external surface of the discharge bag to add a reservoir to the partially cured silicone workpiece. The method also includes curing the partially cured silicone workpiece to create a silicone workpiece. The method also includes masking at least a portion of the absorption bag and the reservoir of the silicone workpiece. The method also includes depositing parylene on the absorption bag, the cannula, the discharge bag, and the reservoir based on the at least portion of the absorption bag and the reservoir being masked.

In an example, the method further includes estimating a consumption of oxygen by live cells. The reservoir is configured to retain the live cells. The cavities in the half molds are dimensioned based on the estimated consumption of the oxygen. Additionally or alternatively, thickness of the silicone defining the absorption bag and the discharge bag is set based on the estimated consumption of oxygen.

In an embodiment, a method of using an implantable medical device is described. The method includes providing the implantable medical device. The implantable medical device includes an absorption bag and a discharge bag connected by a cannula. The implantable medical device also includes a reservoir. The reservoir is external to the discharge bag and has a bottom defined by a portion of the discharge bag, where the portion is permeable to oxygen. The method also includes adding live cells to the reservoir. The method also includes placing at least the reservoir retaining the live cells, the discharge bag, and a portion of the cannula inside a body of a subject. The method also includes securing the implantable medical device in place.

In an example, the method further includes placing the absorption bag at an external surface of a skin of the subject and suturing the absorption bag to the skin. Alternatively, the absorption bag is placed inside the body of the subject and can be sutured to tissue.

In an example, the live cells include isles. The method further includes determining vascular growth around the islets after a period of time and removing the implantable medical device from the body of the subject after the period of time.

A further understanding of the nature and the advantages of the embodiments disclosed and suggested herein may be realized by reference to the remaining portions of the specification and the attached drawings.

BRIEF DESCRIPTION OF THE DRAWINGS

FIGS. 7A-7G illustrate an example of a manufacturing process, in accordance with an embodiment.

DETAILED DESCRIPTION

Figure 1:
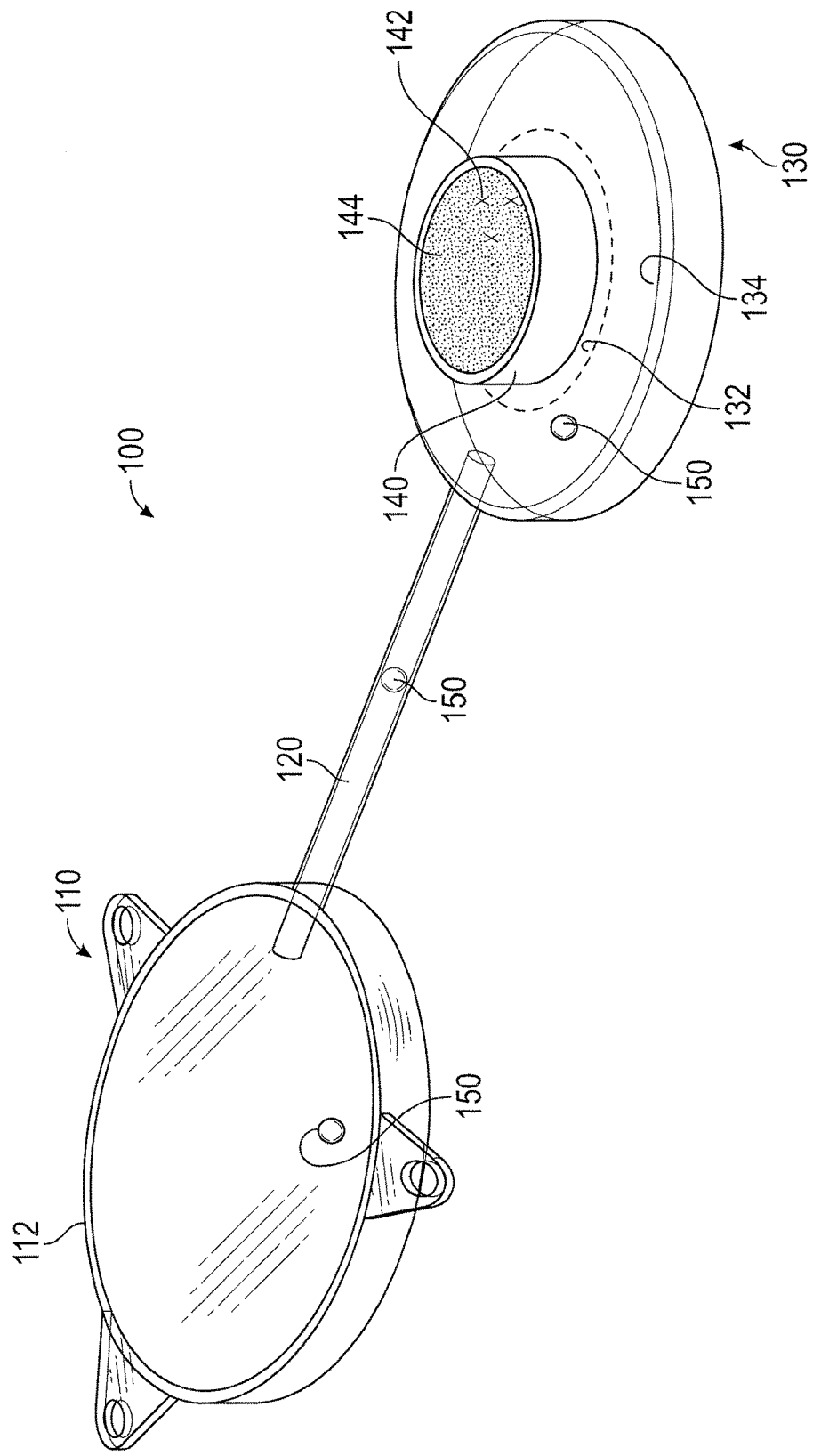
FIG. 1 illustrates an example of an implantable medical device, in accordance with an embodiment.

Implantable medical devices, their methods of manufacture, and methods for their use are described. The implantable medical devices facilitate implanting live tissues in the body and providing nutrients to the live tissues for their survival. The implantable medical devices capture the nutrients from an environment external to the body and/or from within the body and deliver the nutrients to the live tissues.

In an embodiment, an implantable medical device is used to implant islets in a subcutaneous site. The implantable medical device is secured in place for a period of time. A reservoir of the implantable medical device retains the islets and is placed in the subcutaneous site through an incision. Based on a natural concentration gradient of oxygen, the implantable medical device transports oxygen from an oxygen-rich zone into the subcutaneous site, which is an oxygen deficient zone. The transported oxygen is permeated to the islets, thereby providing adequate oxygen flow for their survivals. Over time, vascular growth is achieved around the islets, thereby creating another source of oxygen. When the vascular growth is sufficient for the survival of the islets, the implantable medical device may be removed, whereas the islets may remain in the subcutaneous site.

U.S. Patent Application Publication No. US 2015/0366707, titled "small molecule transport device for drug delivery or waste removal" describes a passive device that facilitates the transportation of small molecules between two locations.

In contrast, embodiments of the present disclosure include an implantable medical device that facilitates implantation of live cells in a body of a subject and targeted supply of small molecules to the live cells for their survival. Specifically, the implantable medical device includes, among other components, a discharge bag. The discharge bag has a particular portion permeable to the small molecules. The live cells are retained at a location that is external to the discharge bag and that corresponds to the particular portion. The small molecules are supplied to the live cells in part through the permeation from the particular portion of the discharge bag. Because the retention location corresponds to the particular portion, the supply is targeted. Further, prior to the implantation, a determination may be made as to the desired amount of the live cells. The consumption of the small molecules by such an amount can be estimated. The estimated consumption can be correlated to a particular size and/or permeation of the implantable medical device such that the appropriate implantable medical device can be obtained and implanted.

In the interest of brevity, an implantable medical device is referred to as a device in the present disclosure. In other words, unless context dictates otherwise, a device as used herein represents a medical device that can be implanted in a body of a subject. The implantation need not be permanent and, instead, can be temporary. The device can be secured in place for the period of the implantation using different techniques, as further described in the next figures.

In the interest of clarity of explanation, embodiments of the present disclosure are described in connection with a device for implanting islets and supplying oxygen to the implanted islets. However, the embodiments are not limited as such. Instead, the device is also usable for implanting other types of live cells and for supplying other types of nutrients to the live cells. Generally, a live cell can be any cell that relies on a nutrient for survival. A nutrient represents a molecule that the cell can consume through cellular metabolism, alone or in combination with other molecules, to survive. Islets are one example of live cells. Oxygen is one example of nutrients.

FIG. 1 illustrates an example of a device 100 in accordance with an embodiment. The device 100 includes an absorption bag 110, a cannula 120, a discharge bag 130, and a means 140 for retaining live cells 142 and providing small molecules 150 to the live cells 142. In an example, the live cells 142 are islets including pancreatic beta cells and the small molecules 150 are molecular oxygen ($O_2$). The small molecules 150 are passively captured by the absorption bag 110 and transported to the discharge bag 130 through the cannula 120. The small molecules 150 are then permeated into the means 140 for consumption by the live cells 142.

In an example, the absorption bag 110 is partially or fully permeable to the small molecules 150. For instance, the entire membrane that forms the absorption bag 110 or only a portion of the membrane is permeable to the small molecules 150. The small molecules 150 permeates to an interior of the absorption bag 150 through the permeable membrane or permeable portion thereof. The absorption bag 110 may also be foldable, rollable, and/or stretchable depending on the membrane.

The cannula 120 includes a thin lumen that connects the interior of the absorption bag 110 to an interior of the discharge bag 130. The cannula 120 is impermeable to the small molecules 150 such that the small molecules 150 are transported between the two interiors through the lumen and without permeation at the cannula 120. For example, the cannula 120 is formed by a membrane coated with a material that renders the cannula 120 impermeable to the small molecules 150. Based on natural concentration gradient of the small molecules 150, transportation occurs from the absorption bag 110 to the discharge bag 130. That is the case when the absorption bag 110 is placed in a region that has a higher concentration of the small molecules 150 relative to the concentration in a region where the discharge bag 130 is placed.

The discharge bag 130 includes a particular portion 132 (e.g., a first portion) that is permeable to the small molecules 150. The remaining portion 134 of the discharge bag 130 (e.g., a second portion) is generally impermeable such the permeation of the small molecules 150 is targeted to occur through the particular portion 132. The discharge bag 130 may also be foldable, rollable, and/or stretchable depending on membrane that forms the discharge bag 130.

The means 140 is external to the discharge bag 130, retains the live cells 142, and supplies the small molecules 150 to the live cells 142 based on the permeation from the permeable portion 132 of the discharge bag 130. Different types of the means exist including, for instance, a reservoir, irregular array of corrugations, an adhesion layer as further described in connection with the next figures. Generally, the live cells 142 belong or are included in a culture 144 retained by the means 140. The culture 144 represent a solution in which the live cells can be placed and that provides a suitable environment for their survivability. A hydrogel is an example of the culture 144. The supply of the small molecules 150 to the live cells 142 can be targeted by properly locating the means 140 relative to the permeable portion 132 of the discharge bag 130. For example, the means 140 is placed on top of the permeable portion 132 and has a bottom surface that is formed by the permeable portion 132, that surrounds the permeable portion 132, or that is approximately surrounded by the permeable portion 132 (e.g., the permeable portion surrounds the bottom surface by a margin that does not exceed 10% (or some other relevant percentage) the total area of the bottom surface)).

Various materials are available and are biocompatible and/or biodegradable. In an example, the absorption bag 110, the cannula 120, the discharge bag 130, and the means 140 are made of biocompatible silicone that has been cured together, i.e., integrally formed. Parylene C coating surrounds cannula 120, the remaining portion 134 of the discharge bag 130 (but not the permeable portion 132), and, optionally, a portion (but not the entire) absorption bag 110. Parylene C is a biocompatible polymer with a permeability rate that is five orders of magnitude lower than silicone. The coating renders the coated portions impermeable to the small molecules 150.

"Permeability" of a material is typically in relation to a size of substance of interest. A Stokes-Einstein radius or a Stokes diameter is a measure of the diffusion properties of a substance. A "Stokes diameter" is an equivalent diameter of a hard sphere that a molecule possesses in terms of its diffusion rate. A molecule can pass through thin materials with pores that have a Stokes diameter that is about 1 to about 5 times the Stokes diameter of the molecule.

"About" includes within a tolerance of ±0.01%, ±0.1%, ±1%, ±2%, ±3%, ±4%, ±5%, ±8%, ±10%, ±15%, ±20%, ±25%, or as otherwise known in the art.

The small molecules 150 diffusion out of the discharge bag 130 into the means 140 lowers the device's 100 internal concentration, and this in turn pulls additional small molecules from a small molecule rich region (e.g., where the absorption bag 110 is located) into the device 100. The concentration gradient will continue to transport small molecules from the rich region into the means 140, thereby providing an adequate flow of the small molecules to the live cells 142.

Dosing and targeted release can be controlled by material properties of the device 100. Controlling the thickness of silicone can determine the permeation rate (dosing). As the absorption bag 110, cannula 120, and discharge bag 130 are integrally formed with the same thickness of silicone, a single adjustment to how much silicone is distributed on a mold can determine permeation rates. Applying impermeable coating to specific portions of the device 100 allows control over the permeation rates and/or locations of the permeations.

The dimensions of the absorption bag 110 and discharge bag 130 can also be adjusted to alter the permeation rate. Generally, the larger the permeable surface area, the larger the permeation rate is (given a same concentration of small molecules). The dimensions and permeable surface areas are application dependent and can be designed for the specific task the device 100 is to perform. For instance, a desired amount of live cells 142 can be determined. The means 140 is dimensioned to hold that amount. An estimated consumption of the small molecules 150 by the amount of the live cells 142 is estimated. The dimensions and permeable surface areas of the absorption bag 110 and discharge bag 130 are set to provide a flow of the small molecules 150 adequate for the estimated consumption. The device 100 is manufactured accordingly.

In addition to controlling the thickness, one may inject into the interior of the device 100 a substance with a high diffusion constant such as perfluorocarbons, air, etc. For example, a perfluorocarbon within the absorption bag 110 and device 100 can increase oxygen solubility (e.g., in the case when the small molecules 150 are oxygen). A hemeprotein, such as a natural, artificial, or autologous hemoglobin or myoglobin, can be added inside the device 100 to increase oxygen transport. A chlorocruorin or a hemocyanin can be added into the absorption bag 110 and other portions of the device 100 to increase oxygen transport. Other substances natural or synthetic that have beneficial properties for small molecule storage or transport may be used.

Other small molecules besides diatomic oxygen can also be captured and transported. The device 100 can be targeted for carbon dioxide ($CO_2$), nitrous oxide ($N_2O$), or other gases. Small molecule proteins and other drugs can be specifically targeted. Any of these 'drugs' may be transported, whether they are classified as a therapeutic agent, waste product, or otherwise.

Figure 2:
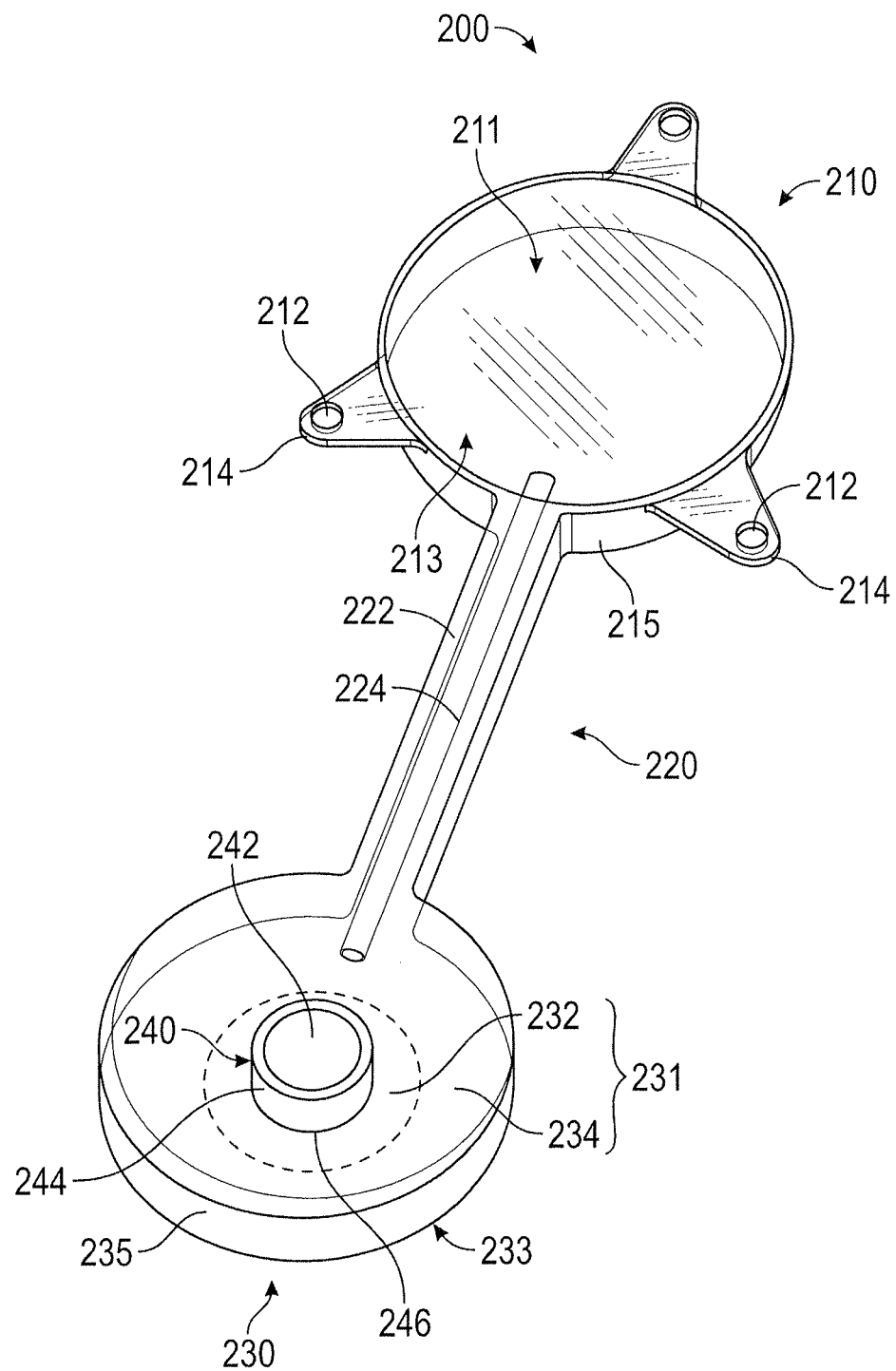
FIG. 2 illustrates an example of an implantable medical device that includes an absorption bag having suture holes, in accordance with an embodiment.

FIG. 2 illustrates an example of a device 200 that includes an absorption bag 210 having suture holes 212, in accordance with an embodiment. In addition to the absorption bag 210, the device 200 includes a cannula 220, a discharge bag 230, and a reservoir 240.

As illustrated, the absorption bag 210 has a cylindrical shape. Other shapes are possible, including a spheroid, a toroid, and the like. A top surface 211, a bottom surface 213, and a side surface 215 define the cylindrical shape. These surfaces are generally, but need not, made of the same material to form an integral membrane that defines the structure of the absorption bag 210. The material is generally permeable to a predefined class of small molecule, such as molecule oxygen ($O_2$). In an example, the material includes NuSil Technology LLC (of Carpinteria, Calif., U.S.A.) MED4-4210, two-part, medical grade silicone in which base and curing agent are mixed at a 10:1 ratio by weight.

Optionally, the bottom surface 213, the side surface 215, and/or other surface areas of the absorption bag 210 are coated with thick parylene (e.g., 2 μm or more of parylene C), rendering these surfaces impermeable to the small molecules. The coating is applied to a surface when, for example, the permeation of the small molecules into the absorption bag 210 is not expected through the surface. For instance, if the absorption bag 210 is attached to the skin of a subject, the bottom surface 213 may sit against the skin and oxygen is not expected to properly diffuse through that surface accordingly, the coating of the thick parylene is applied to the bottom surface 213, rendering that surface impermeable to oxygen.

The device 200 also includes a number of tabs 214. The tabs are made of the same material as the absorption bag 210 (e.g., silicone). In an example, the tabs 214 are spaced symmetrically around the side surface 215. Each of the tabs 214 includes a through hole 212. Through holes 212 are sized for sutures and thus are sometimes called suture holes. These holes can be used to attach and secure the absorption bag 210 to tissue of the subject.

The cannula 220 is also made of the same material as the absorption bag 210 (e.g., silicone). The external surface of the cannula 220 is covered in a thick parylene coating 222 (2 μm or more of parylene C), rendering that surface impermeable to oxygen and/or other small molecules. Enclosed inside the cannula 220 is pliable metal strip 224, such as a biocompatible type three hundred and four stainless steel tube. The tube is pliable so that it can be bent and keep its bent shape. Or it can be re-bent to be straight and then keep its straight shape. In other embodiments, the metal strip 224 may be a thin metal foil, sheet, or solid rod. The metal strip 224 can be bent by a surgeon's hands or by surgical instruments.

The discharge bag 230 has the same or substantially the same shape (a cylindrical shape as illustrated in FIG. 2) and dimensions as the absorption bag 210. The discharge bag 230 is also made of the same material as the absorption bag 210 (e.g., silicone). A top surface 231, a bottom surface 233, and a side surface 235 are made of the material to form an integral membrane that defines the structure of the discharge bag 230.

To allow targeted permeation, the bottom surface 233 and the side surface 235 are covered in a thick parylene coating (2 μm or more of parylene C), rendering these surfaces impermeable to oxygen and/or other small molecules. Further, the top surface 231 is divided into two portions: a first portion 232 and a second portion 234, each defining a surface area. The first portion 232 is not covered with the thick parylene coating and, thus, is permeable to oxygen and/or other small molecules. In contrast, the second portion 234 represents a remaining portion of the top surface 231, is coated with the thick parylene coating, and, thus, is impermeable to oxygen and/or other small molecules.

The reservoir 240 is an example of a means for retaining live cells and for providing oxygen and/or other small molecules to the live cells. The reservoir 240 sits on top of the first, permeable portion 232 of the discharge bag 230. The reservoir includes an opening 242, one or more walls 244, and a bottom surface 246. The opening 242 allows the addition of the live cells into the interior of the reservoir 240. The wall(s) 244 and the bottom surface 246 retain the live cells within that interior. Although a cylindrical shape is illustrated, other shapes and geometries are possible for the reservoir 240, such as a rectangular shape. Oxygen and/or other small molecules to the live cells are supplied through permeation from the bottom surface 246. For example, the bottom surface 246 can be made of the same permeable material as the absorption bag 210 (e.g., silicone). In another example, the bottom surface 246 is formed by the of the first, permeable portion 232 of the discharge bag 230, as opposed to being made with a separate permeable material. In both examples, oxygen and/or other small molecules permeates from the discharge bag 230 into the interior of the reservoir 240 through the first, permeable portion 232 of the discharge bag 230 and the bottom, permeable surface 246 of the reservoir 240.

Figure 3:
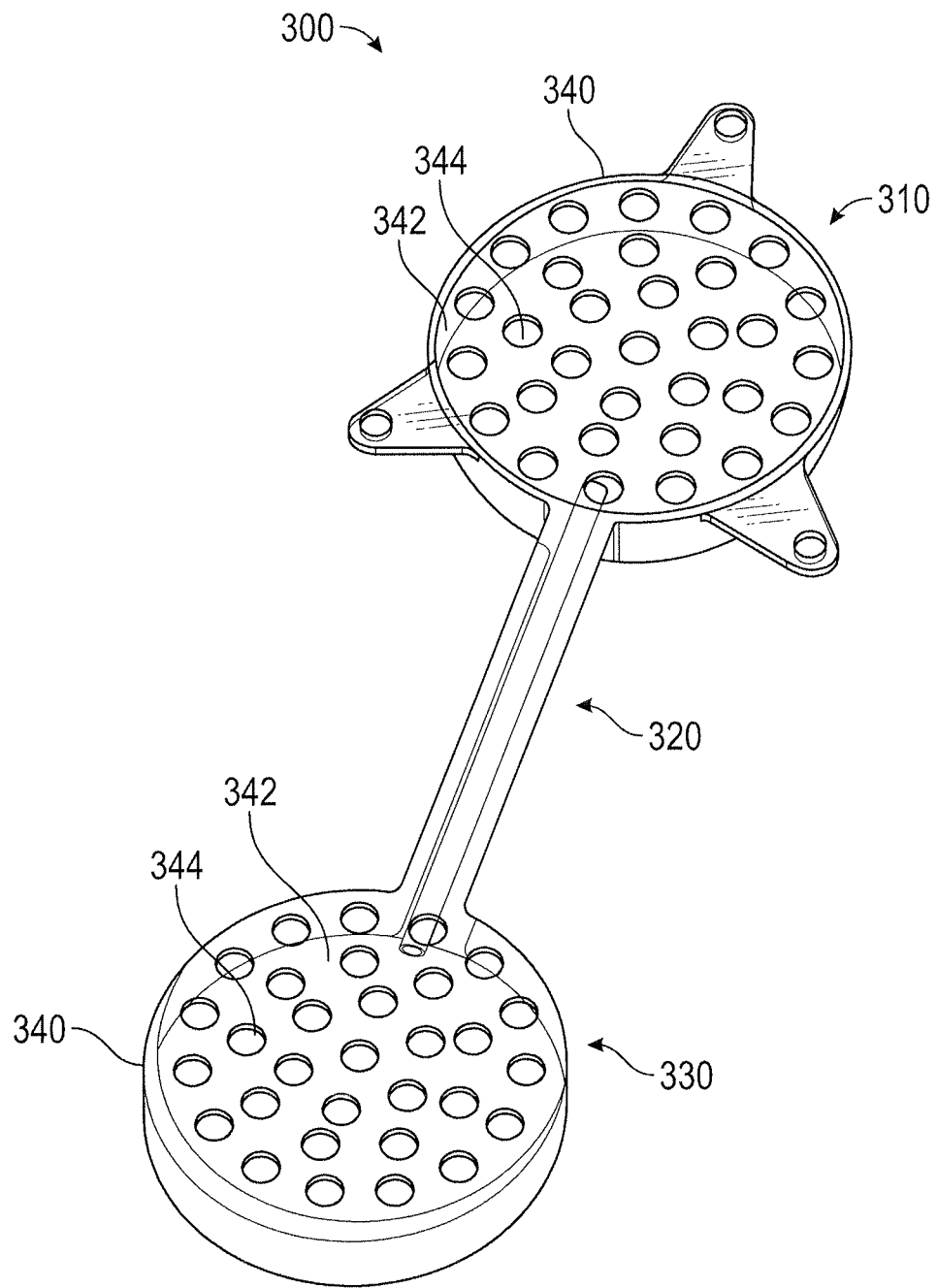
FIG. 3 illustrates an example of an implantable medical device that includes an absorption bag and a discharge bag having a particular configuration, in accordance with an embodiment.

FIG. 3 illustrates an example of a device 300 that includes, in addition to a cannula 320, an absorption bag 310 and a discharge bag 330 having a particular configuration, in accordance with an embodiment. Each of these bags has substantially a cylindrical shape. However, and unlike the plain cylindrical shape illustrated in FIG. 2, the cylindrical shape includes a grill-like configuration. In each of the cylinders, the outer perimeter 340 has a shape that is a torus or a ring. A mesh 342 connects opposite points that belong to the outer perimeter 340. The mesh 342 defines a three dimensional grate for the flow of the oxygen and/or other small molecules. This grate has openings 344 from between top and bottom surfaces of the mesh 342 (or the cylinder) but not into the body of the mesh 342 (or the cylinder). In this configuration, a larger surface area can be achieved given the same footprint of a cylinder relative to the plain cylinder of FIG. 2. Accordingly, a relatively higher permeation rate into and/or out from the device 300 can be achieved.

Although an absorption bag and a discharge bag are illustrated in each of FIGS. 2 and 3 as having the same shape, dimension, and geometry, the embodiments of the present disclosure are not limited as such. Instead, the configurations can differ. For example, the absorption bag can be larger. In another example, while a plain cylindrical shape is used for the discharge bag, a grill-like shape is used for the absorption bag. Generally, the specific configuration for each bag is dependent on the application, such as the type and amount of live cells to be retained, the estimated nutrients consumption for a period of time, among other application parameters.

Figure 4:
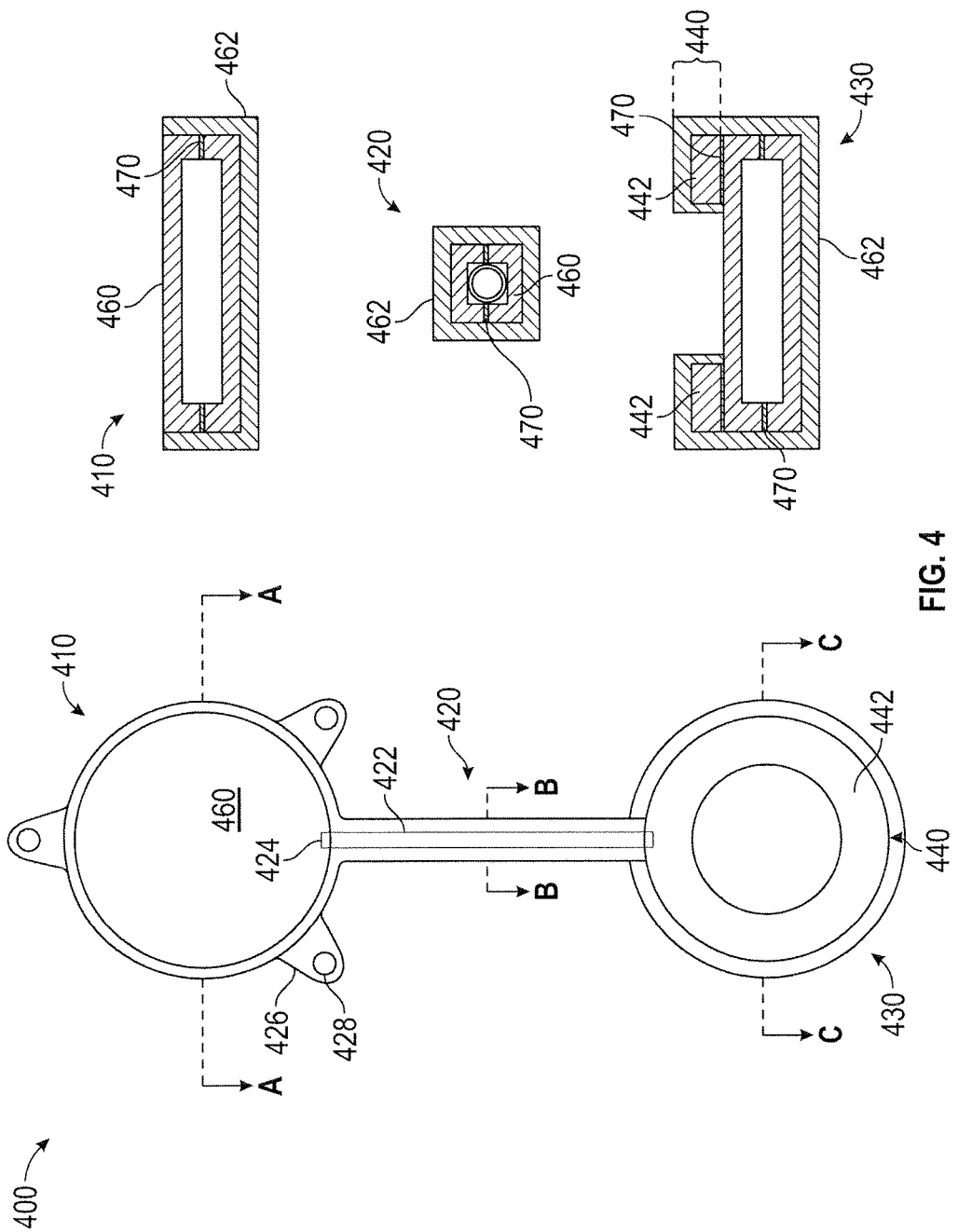
FIG. 4 illustrates a plan view and cross sectional views of an example of an implantable medical device, in accordance with an embodiment.

FIG. 4 illustrates a plan view and cross sectional views of an example of a device 400, in accordance with an embodiment. In the exemplary embodiment, the absorption bag 410 is 10 mm in diameter with 500 μm (micron) walls. The internal height is 720 μm with a ceiling and a floor thickness of 360 μm each, for a total thickness of 1440 μm. The cannula 420 is 10 mm long with a width of 1.5 mm. Like the absorption bag 410, the cannula 420 has an internal height of 720 μm with a ceiling and a floor thickness of 360 μm each, for a total thickness of 1440 μm. The side walls are 400 μm thick.

A tube 422 is placed inside the cannula 420. The tube 422 has an internal diameter of 406.4 μm (0.016 inches) and an outside diameter of 508 μm (0.02 inches). The discharge bag 430 has similar dimensions as the absorption bag 410. Specifically, the discharge bag 430 is 4 is 10 mm in diameter with 500 μm (micron) walls. The internal height is 720 μm with a ceiling and a floor thickness of 360 μm each, for a total thickness of 1440 μm. The absorption bag 410, cannula 420, and discharge bag 430 have squared edges and are all approximately the same height is an indication that they were fabricated together using lithographic techniques.

Permeable material 460, which forms the absorption bag 410, cannula 420, and discharge bag 430 is silicone. A particular silicone that has been shown to be effective is NuSil Technology LLC (of Carpinteria, Calif., U.S.A.) MED4-4210, two-part, medical grade silicone in which base and curing agent are mixed at a 10:1 ratio by weight. To limit permeability, a coating 462 of parylene is applied to specific portions of the absorption bag 410, cannula 420, and discharge bag 430. Specifically, a layer of 10 μm parylene C is applied to the sides and bottom surfaces of the absorption bag 410, thereby forming an envelope that is impermeable to molecular oxygen ($O_2$) and other small molecules. Likewise, a layer of 10 parylene C is applied around the cannula 420 and to sides and bottom surfaces of the discharge bag 430.

Tabs 426 with holes 428 are integrally formed with the device 400. That is, the silicone of these appurtenances are at least partially co-cured with that of absorption bag 410, cannula 420, and discharge bag 430. As will be detailed below, a thin layer of uncured silicone 470 is spread between partially-cured halves of the device 400 before fully curing the device's silicone material. Further, uncured silicone 470 is spread in cannula 420 before the metal tube 422 is placed therein. The metal tube 422 keeps lumen 424 free from flowing silicone while curing.

In addition, a reservoir 440 is attached to a top surface of the absorption bag 410. The reservoir 440 has a cylindrical shape, with an internal diameter of 6.35 mm and a height of 500 μm. The wall 442 of the reservoir 440 is about 1.825 mm thick. The reservoir 440 centered around the center of the top surface of the discharge bag 430. Its wall 442 is attached to the top surface absorption bag 410 via the uncured silicone 470 and ends at the edge of the top surface. The bottom surface of the reservoir 440 is formed by the top surface of the absorption bag 410 and, thus, is made of silicone, which is permeable to molecular oxygen ($O_2$) and other small molecules. The wall 442 is coated with a layer of 10 μm parylene C.

The reservoir has volume of 15.27 mm$^3$ suitable for retaining about 1,500 IEQ of islets in hydrogel, where one IEQ is considered equivalent to a pancreatic islet with a diameter of 150 μm. The dimensions and permeability of the absorption bag 410, cannula 420, and absorption bag 430 provides sufficient oxygen for the 1,500 IEQ of islets such that the islets survive and grow over a period of at least two weeks given the oxygen flow through the device 400.

Other dimensions of the medical device 400 are possible. The specific shape, geometry, membrane thickness, and permeation of the absorption bag 410, cannula 420, discharge bag 430, and reservoir 440 are application dependent. Generally, the internal diameter of the reservoir 440 is in the range of 1 mm to 20 mm and the height of its wall falls in the range of 100 µm to 1 mm. Similarly, each of the absorption bag 410 and the discharge bag 430 has an internal diameter in the range of 2 mm to 30 mm and having an internal height in the range of 200 µm to 2 mm. The cannula 420 is sized such that the width of its lumen 424 is smaller than the diameter of the absorption bag 410. For instance, this width falls in the range of 0.1 mm to 5 mm.

Figure 5:
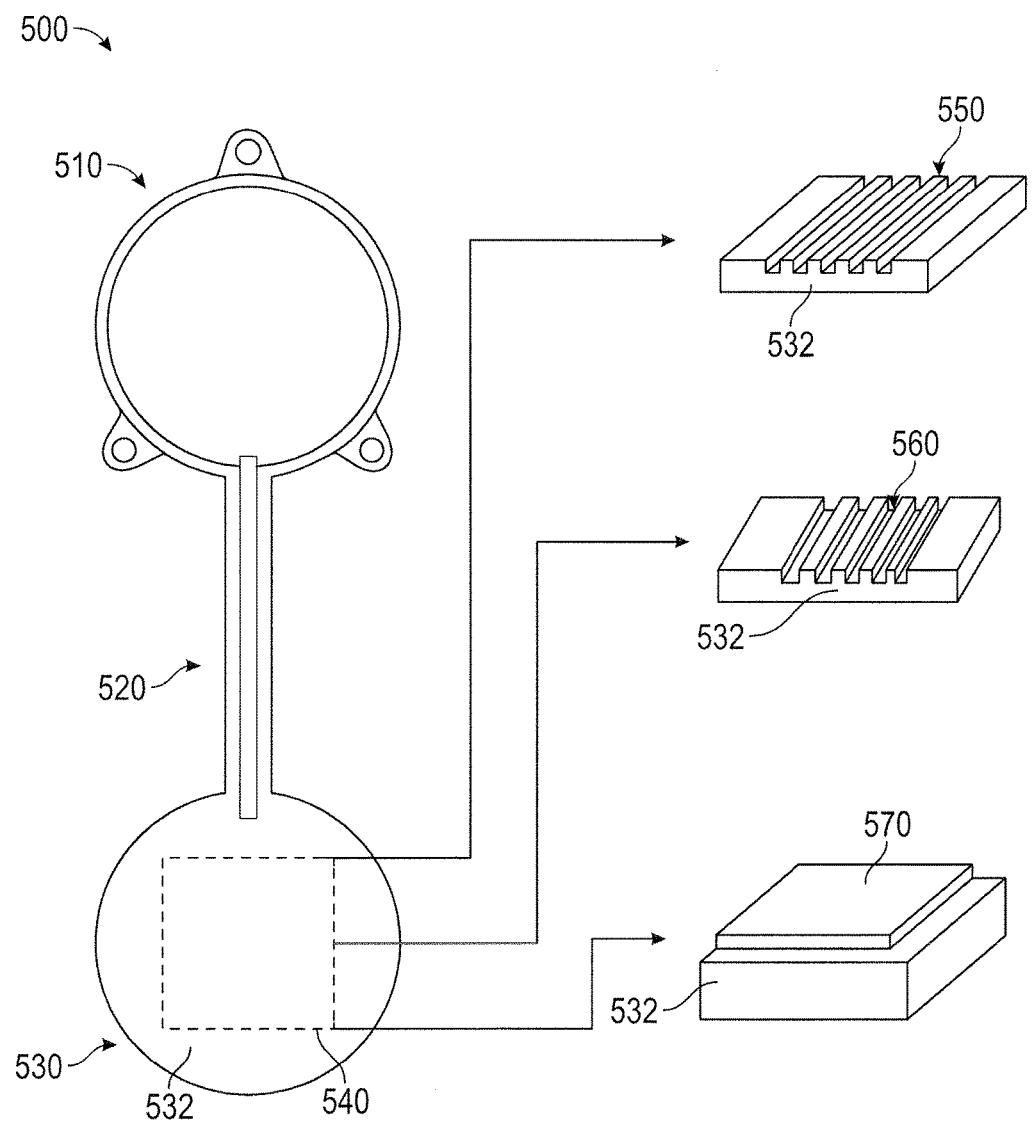
FIG. 5 illustrates examples of retaining live cells on an external surface of a discharge bag, in accordance with an embodiment.

FIG. 5 illustrates examples of retaining live cells on an external surface of a discharge bag, in accordance with an embodiment. Whereas FIG. 4 illustrates a reservoir 440 as one exemplary embodiment, FIG. 5 illustrates additional exemplary embodiments for the retaining and for providing nutrients to the live cells.

In FIG. 5, a device 500 includes an absorption bag 510, a cannula 520, and a discharge bag 530. A means 540 is located on a top surface 532 of the discharge bag 530. The means 540 retains an amount of the live cells and provides oxygen and/or other small molecules as nutrients to the live cells based on permeation through the top surface 532. Three specific configurations of the means 540 are illustrated.

In a first configuration, the means 540 includes a pattern of corrugations 550 that are disposed on the top surface 532. Specifically, the corrugations 550 are formed on an external surface of the first portion of the discharge bag 530 (e.g., on the external side of the top surface 532). The pattern is regular (e.g., repetitive as a function of height, width, and/or length) and has a specific geometry. FIG. 5 illustrates a repetitive cuboid geometry. Each cuboid has a square base and a length. The width (and height) of the square is in the range of one eight to one half of the thickness of the top surface 532 (e.g., range of 45 µm to 180 µm for a 360 µm thickness). The length of the cuboid is in the range of one fourth to three fourth of the diameter of the discharge bag 530 (e.g., range of 180 µm to 540 µm for a 720 µm diameter). Other repetitive, three dimensional geometries are also possible. Geometries having squared edges and approximately the same height (e.g., such as cuboids) are an indication that the corrugations 550 were fabricated using lithographic techniques. Specifically, the half molds for creating the absorption bag include corresponding cavities to form the corrugations 550.

In a second configuration, the means 540 includes array of corrugations 560 that are disposed on the top surface 532. Like the first configuration, the corrugations 560 are formed on an external surface of the first portion of the discharge bag 530 (e.g., on the external side of the top surface 532). However, the array here has an irregular pattern, such as one with random heights, widths, and/or lengths. Generally, the overall dimensions of the array have a length and width in the range of one fourth to three fourth of the diameter of the discharge bag 530, and a height in the range of one eight to one half of the thickness of the top surface 532. Using a random pattern may simplify, relative to the first configuration, the process of creating the corrugations 560.

In a third configuration, the means 540 includes an adhesion layer 570 that is disposed on the top surface 532. Generally, the live cells are included in a culture, such as hydrogel. The adhesion layer 570 is disposed between a first portion of the discharge bag 530 (e.g., on the external side of the top surface 532) and a second portion of the culture (e.g., on the external side of the bottom surface of the hydrogel). The adhesion layer 570 provides bonding, such as covalent bonding, between the top surface 532 and the culture and is permeable to the oxygen and/or small molecules. Depending on the type of the material that forms the top surface 532 and/or the hydrogel, the adhesion layer 570 can be defined and can be separate or integrated with the external side of the top surface 532 and/or the hydrogel. For instance, fibroblasts, a type of cells found in connective tissue, are cultured and stretched, and then applied as a coating between the two external sides.

In the above configurations, the means 540 mainly consists of an interface (e.g., corrugations or adhesion layer) for retaining the culture of the live cells, whereas the reservoir 440 FIG. 4 defines a well. In such configurations, the culture itself needs to have a solid-like state such that it remains attached to the top surface through the interface of the means 540. In an example, the culture includes equal parts of vinyl sulfone (VS) functionalized saccharide-peptide copolymer and cysteine (Cys) functionalized saccharide-peptide copolymer. When these two parts are initially mixed, the culture is liquid and can be deposited on the means 540 (and/or the reservoir 440). Shortly thereafter, the culture solidifies into a hydrogel.

Figure 6:
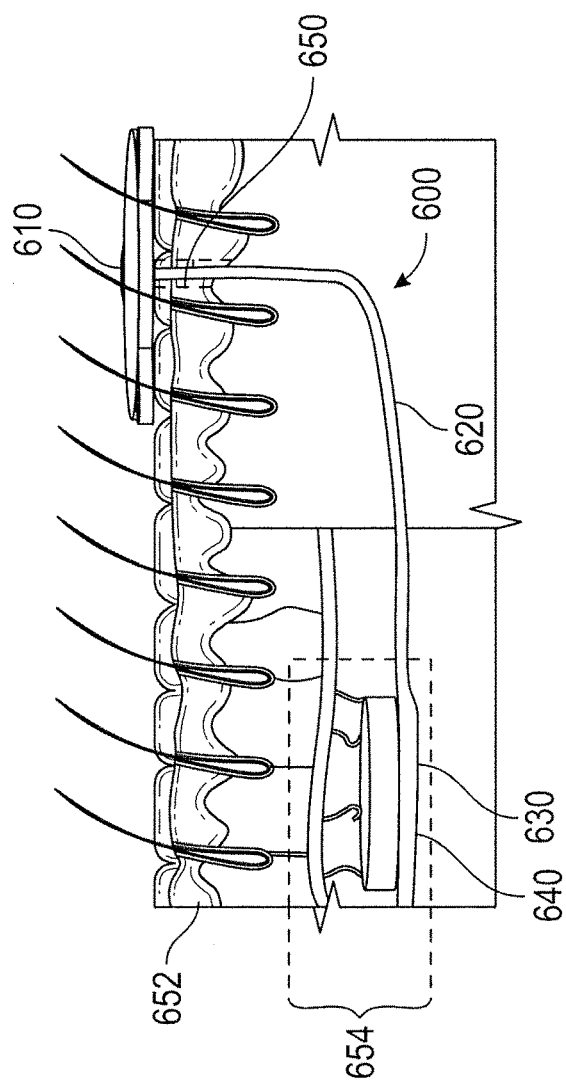
FIG. 6 illustrates an example of a subcutaneous implantation, in accordance with an embodiment.

FIG. 6 illustrates an example of a subcutaneous implantation, in accordance with an embodiment. The implantation is subcutaneous in the abdomen of a subject. An incision 650 is made in the abdomen. An absorption bag 610 of a device 600 sits on the exterior of the abdomen, such as on external side of the epidermis 652. A cannula 620 and a discharge bag 630 of the device 600 are inserted in the subcutaneous area 654 through the incision 650. A reservoir 640 attached to and external to the discharge bag 630 retains hydrogel that contains islets. The reservoir 640 is positioned such that its opening is towards the epidermis 652. Hence, the device 600 absorbs oxygen from the ambient air external to the abdomen (at about 160 mmHg, depending on the external environment). The oxygen is transported to the islets retained in the reservoir 640.

Simulation of the subcutaneous implantation demonstrates that oxygen can be provided to the islets at a partial pressure ($pO_2$) of 55.04 mmHg on average, which is sufficient for the islet survival. In comparison, absent the device 600, the oxygen would be provided at an average of 3.70 mmHg of partial pressure, which is insufficient for the islet survival.

Further, in lab experimentation, the device 600 is tested by immersing the hydrogel containing the islets to an anoxic culture medium. An oxygen sensor was inserted in the hydrogel. The lab experimentation demonstrated a steady $pO2$ at the center of top surface of the discharge bag 630 (e.g., the center of the bottom surface of the reservoir 640) to be between 118 mmHg and 126 mmHg, which demonstrated that the device 600 is highly efficient in terms of extra oxygen supply.

FIGS. 7A-7G illustrate an example of a manufacturing process, in accordance with an embodiment.

Figure 7A:
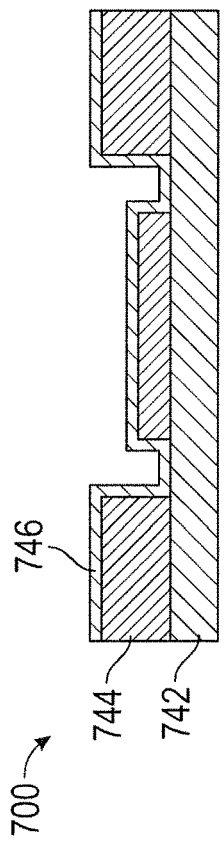

In FIG. 7A, a half mold 700 includes silicon substrate 742 with a dry film photoresist 744 patterned in the shape (e.g., half cylinders connected by a half cuboid) of the final device.

The photoresist was masked and exposed to visible or ultraviolet (UV) light or other electromagnetic radiation and then developed to create the half molds. Because such masks can be easily altered, a device can be custom made using custom molds. The molds include cavities sized to create a specific configuration of the device. In turn, the specific configuration can be set to retain a particular amount of live cells over a time period and expected consumption of nutrients by the live cells, where the nutrients are to be supplied through the device.

The illustrated half mold 700 defines the top half of the device. A mirror half mold can be used for the bottom half of the device. The half mold 700 is coated entirely with coating 746 of parylene C in order to reduce adhesion between silicone and the mold and thus increase the mold's releasability. Although not illustrated, a section of the half mold 700 can also include additional cavities to define corrugations on an external side of a top surface of a discharge bag.

Figure 7B:
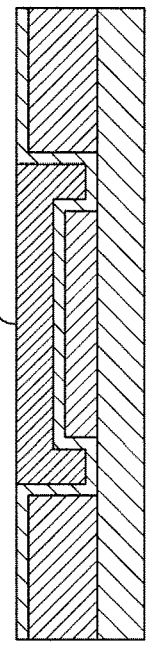

In FIG. 7B, uncured silicone 748 is dabbed and brushed upon the half mold 700 so as to coat the bottom and sides. It is then partially cured at 65° C. for 30 minutes. A similar application is made for the mirror, bottom half mold.

In FIG. 7C, partially cured silicone 748 is peeled from the half mold 700. Its joining edges are then coated with uncured silicone 750. A pliable tube of malleable, ductile metal is cut to a desired length and inserted in the cannula, "handle section" of the device.

In FIG. 7D, a mold 760 includes silicone substrate 762 with dry film photoresist 764 and is patterned to define a wall of a reservoir. The reservoir can be adjoined to a top surface of a discharge bag of the device. The photoresist is masked, exposed, and developed similarly to that of the photoresist for the half mold 700. The half mold 760 is also coated with parylene C 766.

In FIG. 7E, uncured silicone 768 is dabbed and brushed upon the mold 760 so as to coat the bottom and sides. It is then partially cured at 65° C. for 30 minutes.

In FIG. 7F, partially cured silicone 768 is peeled from the mold 760. Its joining edges are then coated with uncured silicone 750.

In FIG. 7G, the complementary partially cured silicone are joined along the joining edges. For example, the top and bottom partially cured silicones halves are aligned and joined, with the metal tube in between the halves to form an assembly that includes sections for an absorption bag, cannula, and discharge bag. The partially cured silicone wall 768 is aligned and joined to a top surface of the section corresponding to the discharge bag. The assembly is fully cured at 100° C. for 8 hours. A portion of or the entire absorption bag and the bottom of the reservoir are then masked, and the assembly is placed in a chemical vapor deposition (CVD) chamber for depositing parylene around the unmasked portions of the device. A layer 770 of parylene C (e.g., about 10 μm) ensures that the cannula is impermeable to oxygen and/or other small molecules.

Figure 8:
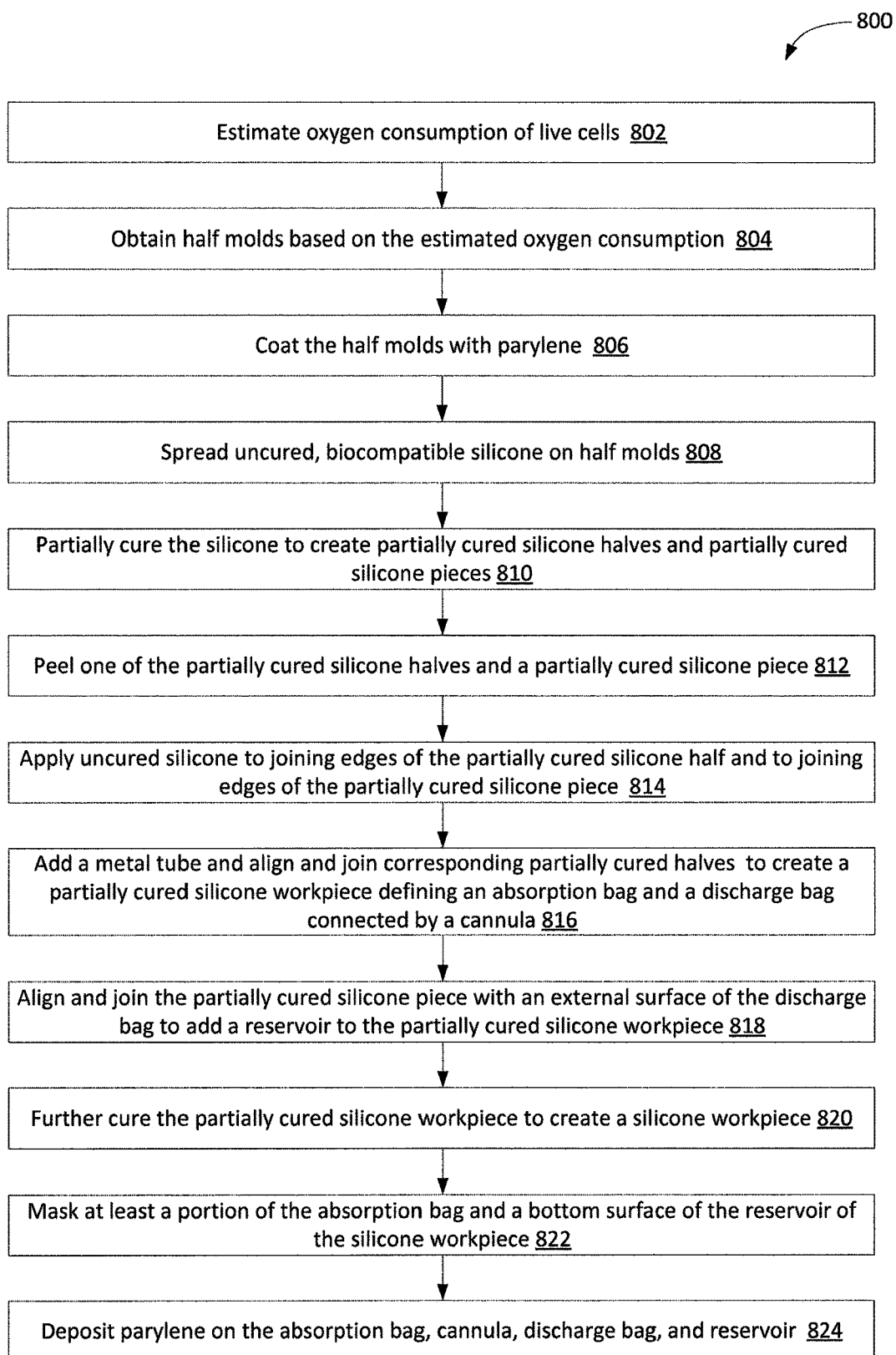
FIG. 8 is a flowchart illustrating an example method of manufacturing, in accordance with an embodiment.

FIG. 8 is a flowchart illustrating an example method of manufacturing 800, in accordance with an embodiment In operation 802, consumption of small molecules by live cells is evaluated. For example, the oxygen consumption of the live cells for their survival and growth over a period of time is estimated. The estimation can involve utilizing a lookup table. The lookup table correlates consumption to quantity of the live cells. For example, the lookup table documents the oxygen rate needed to grow 1,500 IEQ of live cells for a period of two weeks. The lookup table can be developed through experimentation and/or modeling. In experimentation, different quantities of live cells can be cultured. Oxygen sensors can be added to the cultures and used to determine the necessary oxygen rate. In modeling, the consumption rate can be modeled following Monod kinetics, where $$\mu = \frac{\mu_m S}{K_s + S},$$

where "$\mu$" is the growth rate, "$\mu_m$" is the maximum growth rate (an empirical value), "$K_s$" is the Monod constant (an empirical value) of the substrate (e.g., the culture), and "$S$" is the limiting growth of the substrate. For oxygen, "$\mu$" can be also expressed as $$\mu = \frac{C_{DO}}{K_{DO} + C_{DO}},$$

where "$C_{DO}$" is the concentration of dissolved oxygen and, "$K_{DO}$" is the Monod constant of the dissolved oxygen.

In operation 804, half molds are obtained based on the estimated consumption of the small molecules (e.g., the estimated oxygen consumption). For example, a particular oxygen consumption may dictate a particular configuration (e.g., shape, size, and/or geometry) of a device that includes an absorption bag, a cannula, a discharge bag, and a reservoir (or other means for retaining live cells and providing nutrients thereto). The cannula connects the absorption bag and the discharge bag. Half molds are created using lithography other techniques, where the half molds correspond to the absorption bag, cannula, and discharge bag. Molds are similarly created for the reservoir. Cavities in the half molds and molds are defined to meet the particular configuration of the device. Additionally or alternatively, the thickness of material applied to the half molds and molds to define permeable and impermeable membranes is controlled according to the particular configuration.

In operation 806, the half molds are coated with parylene C. Similarly, the molds of the reservoir are also coated with parylene C.

In operation 808, uncured, biocompatible silicone is spread on the half molds. Similarly, uncured, biocompatible silicone is spread on the molds.

In operation 810, the silicone on the half molds is partially cured to create partially cured silicone halves. The silicone halves will define the absorption bag, cannula, and discharge bag. Similarly, the silicone on the molds is partially cured to create partially cured silicone pieces. The silicone pieces will define the reservoir.

In operation 812, one of the partially cured halves is peeled from one of the half molds. The peeling is facilitated by the coating of parylene C. Similarly, one of the partially cured silicone pieces is peeled from on the molds.

In operation 814, uncured, biocompatible silicone is applied to the peeled, partially cured silicone halves. For example, the uncured, biocompatible silicone is applied to joining edges of the peeled silicone half. Similarly, uncured, biocompatible silicone is applied to joining edges of the peeled, partially cured silicone piece.

In operation 816, a metal tube is added to the peeled silicone half. Thereafter, the peeled silicone half is aligned and joined with a corresponding partially cured silicone half to create a partially cured silicone workpiece. The joining edges are used. The partially cured silicone workpiece defines the absorption bag, cannula, and discharge bag. The cannula contains the metal tube.

In operation 818, the peeled, partially cured silicone piece is aligned and joined with an external surface of the discharge bag to add, to the partially cured silicone workpiece, the reservoir (e.g., a silicone reservoir having a silicone wall defined by the peeled, partially cured silicone piece and having a bottom surface defined by the external surface of the discharge bag). The joining edges of the peeled, partially cured silicone piece are used.

In operation 820, the partially cured silicone workpiece is further cured to create a silicone workpiece. The silicone workpiece includes the absorption bag, cannula, discharge bag, and reservoir.

In operation 820, at least a portion of the absorption bag and a bottom surface of the reservoir of the silicone workpiece are masked. For example, a top surface of the absorption bag may be desired to remain permeable to the small molecules (e.g., the oxygen). Similarly, the bottom surface of the reservoir interfaces with the top surface of the discharge bag and may be desired to remain permeable such that the small molecules permeate from the discharge bag into the reservoir through that interface. Accordingly, these portions are masked.

In operation 822, parylene is deposited on the unmasked portions of absorption bag, cannula, discharge bag, and reservoir. The coating reduces permeability of these portions.

Figure 9:
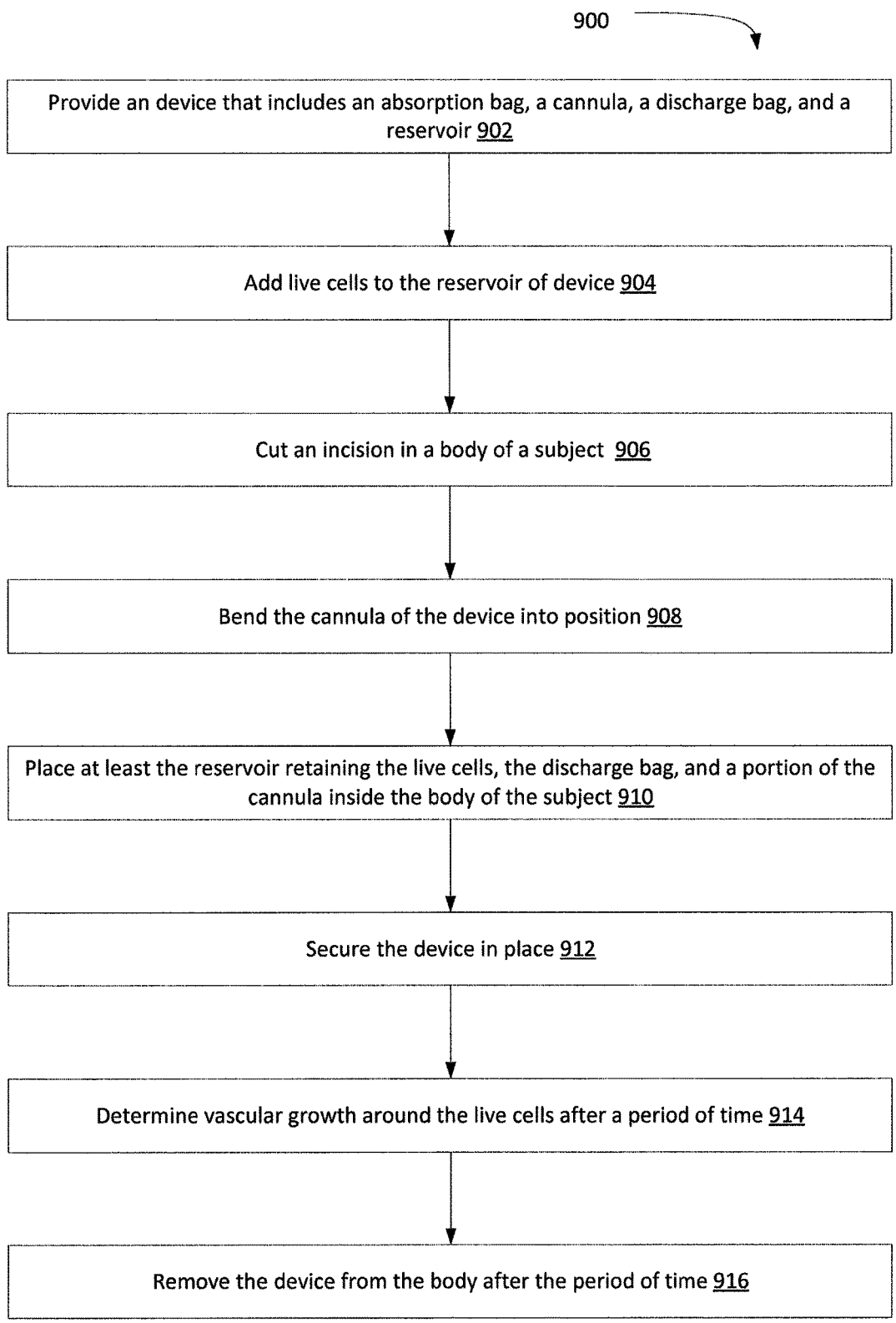
FIG. 9 is a flowchart illustrating an example method of use, in accordance with an embodiment.

FIG. 9 is a flowchart illustrating an example method of use 900, in accordance with an embodiment.

In operation 902, a device is provided, where the device includes an absorption bag, a cannula, a discharge bag, and a reservoir. The cannula includes a metal tube and connects the absorption bag and the discharge bag. The reservoir is external to the discharge bag and is attached to a surface of the discharge bag.

In operation 904, live cells are added to the reservoir of the device. For example, parts of vinyl sulfone (VS) functionalized saccharide-peptide copolymer and cysteine (Cys) functionalized saccharide-peptide copolymer are mixed to form a culture. The live cells are added to the culture. The culture is then moved to a syringe. The syringe is used to add the culture to the reservoir.

In operation 906, an incision is cut in a body of a subject. For example, a ten millimeter incisions is cut into the abdomen of the subject.

In operation 908, the cannula with the pliable metal tube is bent into position.

In operation 910, at least the reservoir retaining the live cells, the discharge bag, and a portion of the cannula are placed inside the body. In an example, the reservoir, discharge bag, and portion of the cannula are pulled through the incision. For instance, these components of the device are placed in a subcutaneous site in the abdomen area.

In operation 912, the device is secured in place. In an example, the absorption bag is placed outside of the body. In another example, the absorption bag in subcutaneous site, but at a location with relatively higher oxygen concentration (or a relatively higher concentration of other small molecules usable as nutrients for the live cells). In both example, the device can be secured in place by suturing the absorption bag to surrounding skin or tissue.

In operation 914, vascular growth around the live cells can be determined after a period of time. In an example, the vascular growth can be expected over time. In another example, a probe is used to determine the vascular growth.

In operation 916, the device is removed from the body after the period of time. For example, if the vascular growth is satisfactory (e.g., provides adequate oxygen flow or an adequate source of nutrients to the live cells), the device is removed. Removing the device includes removing the absorption bag, the cannula, and the discharge bag. Optionally, the reservoir is removed. However, the live cells are not removed and are retained in the body. A surgical tool can be used to cut an incision in the body and remove any of the desired components of the device.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" includes within a tolerance of ±0.01%, ±0.1%, ±1%, ±2%, ±3%, ±4%, ±5%, ±8%, ±10%, ±15%, ±20%, ±25%, or as otherwise known in the art. "Substantially" refers to more than 66%, 75%, 80%, 90%, 95%, or, depending on the context within which the term substantially appears, value otherwise as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An implantable medical device, comprising:
   an absorption bag that comprises at least one portion permeable to oxygen and that defines an interior;
   a discharge bag that comprises a first portion permeable to the oxygen and a second portion impermeable to the oxygen and that defines an interior;
   a cannula that comprises a lumen and a portion impermeable to the oxygen, wherein the lumen of the cannula connects the interior of the absorption bag to the interior of the discharge bag; and
   a reservoir that is external to the discharge bag, is on the first portion of the discharge bag, and comprises a wall, an opening, and a bottom, wherein:
      the wall is impermeable to the oxygen and is attached to the first portion of the discharge bag,
      the bottom is defined by the first portion of the discharge bag,
      the reservoir is configured to retain live cells received through the opening and to provide the oxygen to the live cells based on oxygen permeation through the first portion of the discharge bag, and
      the discharge bag and the absorption bag are dimensioned based on an expected oxygen consumption by the live cells.

2. The implantable medical device of claim 1, wherein the live cells belong to a culture, and wherein the culture is retained by the reservoir.

3. The implantable medical device of claim 2, wherein the culture comprises a hydrogel.

4. The implantable medical device of claim 3, wherein the hydrogel comprises vinyl sulfone and cysteine, and wherein the live cells comprise islets.

5. The implantable medical device of claim 1, wherein the absorption bag, the cannula, the discharge bag, and the reservoir are integrally formed with one another of silicone, and wherein the portion of the cannula impermeable to the oxygen is formed by a coating of parylene over the silicone.

6. The implantable medical device of claim 5, wherein the second portion of the discharge bag is impermeable to the oxygen based on a coating of parylene over the silicone that defines the second portion, and wherein the coating of the parylene does not extend to the first portion of the discharge bag permeable to the oxygen.

7. The implantable medical device of claim 5, wherein the wall of the reservoir comprises a coating of parylene over the silicone that defines the wall, and wherein the wall of the reservoir are impermeable to the oxygen based on the coating of parylene.

8. The implantable medical device of claim 5, wherein a portion of the absorption bag is impermeable to the oxygen based on a coating of parylene over the silicone that defines the portion of the absorption bag.

9. The implantable medical device of claim 1, wherein the reservoir has a cylindrical shape.

10. The implantable medical device of claim 9, wherein an internal diameter of the reservoir is in the range of 1 mm to 20 mm.

11. The implantable medical device of claim 1, wherein the wall of the reservoir has a height that falls in the range of 100 μm to 1 mm.

12. An implantable medical device, comprising: an absorption bag that comprises at least one portion permeable to a predefined class of small molecules and that defines an interior;
   a discharge bag that comprises a first portion permeable to the small molecules and a second portion impermeable to the small molecules and that defines an interior;
   a cannula that comprises a lumen and a portion impermeable to the small molecules, wherein the lumen of the cannula connects the interior of the absorption bag to the interior of the discharge bag; and
   a means for retaining live cells and for providing the small molecules to the live cells based on permeation through the first portion of the discharge bag, wherein the means is external to the discharge bag, and located on the first portion of the discharge bag.

13. The implantable medical device of claim 12, wherein the discharge bag and the absorption bag are dimensioned based on an expected consumption of the small molecules by the live cells.

14. The implantable medical device of claim 12, wherein the means for retaining the live cells and for providing the small molecules to the live cells comprises a reservoir, wherein the reservoir is external to the discharge bag and comprises a wall, an opening, and a bottom, wherein the wall is impermeable to the small molecules and is attached to the first portion of the discharge bag, wherein the bottom is defined by the first portion of the discharge bag.

15. The implantable medical device of claim 12, wherein the means for retaining the live cells and for providing the small molecules to the live cells comprises an irregular array of corrugations that are disposed on an external side of the first portion of the discharge bag.

16. The implantable medical device of claim 12, wherein the means for retaining the live cells and for providing the small molecules to the live cells comprises a pattern of corrugations that are disposed on an external side of the first portion of the discharge bag.

17. The implantable medical device of claim 12, wherein the live cells are disposed in a hydrogel, and wherein the means for retaining the live cells and for providing the small molecules to the live cells comprises an adhesion layer between the first portion of the discharge bag and the hydrogel.

* * * * *